(12) United States Patent
Racenet et al.

(10) Patent No.: US 9,887,562 B2
(45) Date of Patent: Feb. 6, 2018

(54) SMART CART

(71) Applicant: Covidien LP, Mansfield, MA (US)

(72) Inventors: David Racenet, Killingworth, CT (US); Danyel Racenet, Killingworth, CT (US); Parag Sapre, Yardley, PA (US); Francesco Alfieri, Lincoln, RI (US)

(73) Assignee: Covidien LP, Mansfield, MA (US)

( * ) Notice: Subject to any disclaimer, the term of this patent is extended or adjusted under 35 U.S.C. 154(b) by 134 days.

(21) Appl. No.: 14/064,388

(22) Filed: Oct. 28, 2013

(65) Prior Publication Data

US 2014/0152238 A1 Jun. 5, 2014

Related U.S. Application Data

(60) Provisional application No. 61/732,640, filed on Dec. 3, 2012.

(51) Int. Cl.
*H02J 7/00* (2006.01)
*A61B 50/18* (2016.01)
(Continued)

(52) U.S. Cl.
CPC ............ *H02J 7/0042* (2013.01); *A61B 50/10* (2016.02); *A61B 50/13* (2016.02); *A61B 50/18* (2016.02);
(Continued)

(58) Field of Classification Search
CPC ............... H02J 7/0042; A61B 19/0248; A61B 2019/0249; A61B 2019/025; A61B 2019/0252; A61B 2019/0254
(Continued)

(56) References Cited

U.S. PATENT DOCUMENTS

| | | | | |
|---|---|---|---|---|
| 1,944,394 A | * | 1/1934 | Bales | A47B 47/03 |
| | | | | 126/39 B |
| 3,168,954 A | * | 2/1965 | Von Herrmann | A47G 1/21 |
| | | | | 211/50 |

(Continued)

FOREIGN PATENT DOCUMENTS

| CN | 1899211 A | 1/2007 |
|---|---|---|
| CN | 102088883 A | 6/2011 |

(Continued)

OTHER PUBLICATIONS

Chinese Office Action dated May 5, 2017 issued in corresponding Chinese Application No. 2013106421052.

(Continued)

*Primary Examiner* — Andrew M Roersma (57) ABSTRACT

An interactive surgical device storage and supply cart is provided and includes a top storage assembly having multiple storage containers for various size product packages, a bottom storage assembly having drawers to retain larger packages of sterilized devices and an intermediate shelf having storage trays for frequently used items. One or more batter chargers are provided on the cart to supply fully charged batteries. A docking station is provided on the cart to receive computers for inventory management and display instructional material. The docking station also can receive communication devices for consultation with outside sources in real time. Additionally, a power strip is provided to power the battery charger (s) and docking station as well as other auxiliary, powered devices and instruments.

15 Claims, 12 Drawing Sheets

(51) Int. Cl.
*A61B 50/10* (2016.01)
*A61B 50/13* (2016.01)

(52) U.S. Cl.
CPC ... *A61B 2050/105* (2016.02); *A61B 2050/185* (2016.02); *F04C 2270/0421* (2013.01)

(58) Field of Classification Search
USPC .................. 320/107; 312/196, 209, 249.8, 312/249.11–249.13
See application file for complete search history.

(56) References Cited

U.S. PATENT DOCUMENTS

| | | | | |
|---|---|---|---|---|
| 3,995,674 | A * | 12/1976 | Crawford | A47B 81/06 150/165 |
| 4,120,549 | A * | 10/1978 | Bureau | B25H 3/00 280/47.35 |
| 4,373,761 | A * | 2/1983 | Hansberry, Jr. | B25H 5/00 182/132 |
| 5,011,240 | A * | 4/1991 | Kelley | A47B 31/00 312/249.12 |
| 5,013,103 | A * | 5/1991 | Addison | A47B 21/00 248/316.3 |
| 5,016,948 | A * | 5/1991 | Welch | A47B 88/0451 211/126.15 |
| 5,399,007 | A * | 3/1995 | Marconet | A61G 15/14 312/209 |
| 5,423,651 | A * | 6/1995 | Dinverno | B25H 3/00 280/47.35 |
| 5,518,310 | A | 5/1996 | Ellman et al. | |
| 5,536,084 | A | 7/1996 | Curtis et al. | |
| 5,702,115 | A * | 12/1997 | Pool | A61G 12/001 280/47.35 |
| 6,053,587 | A * | 4/2000 | Boerder | A47B 83/045 280/30 |
| 6,086,073 | A * | 7/2000 | Tisbo | B25H 1/02 280/47.26 |
| 6,152,048 | A * | 11/2000 | Vander Park | A47B 17/003 108/50.02 |
| 6,315,308 | B1 | 11/2001 | Konopka | |
| 6,339,732 | B1 * | 1/2002 | Phoon | A61J 7/0084 700/237 |
| 6,626,445 | B2 | 9/2003 | Murphy et al. | |
| 6,663,202 | B2 * | 12/2003 | Spann | A61G 12/001 312/241 |
| 6,746,091 | B2 | 6/2004 | Friar et al. | |
| 6,831,225 | B2 | 12/2004 | Chandler | |
| 6,876,902 | B2 | 4/2005 | Nikolich | |
| 6,976,744 | B2 * | 12/2005 | Hay | A47B 97/00 312/249.13 |
| 7,009,840 | B2 | 3/2006 | Clark et al. | |
| 7,156,475 | B2 * | 1/2007 | Gloger, Jr. | A47B 81/00 312/216 |
| 7,581,708 | B2 | 9/2009 | Newkirk | |
| 7,665,811 | B2 * | 2/2010 | Johanning | A61G 12/001 312/209 |
| 7,800,914 | B2 | 9/2010 | Dully | |
| 7,806,376 | B2 | 10/2010 | Song et al. | |
| 7,809,470 | B2 | 10/2010 | Shoenfeld | |
| 8,075,071 | B1 * | 12/2011 | Whittall | A47B 23/043 312/209 |
| 8,084,992 | B2 * | 12/2011 | Scheffy | B25H 3/02 312/223.1 |
| 8,106,746 | B2 | 1/2012 | Maltseff et al. | |
| 8,109,527 | B2 | 2/2012 | Bustle et al. | |
| 8,157,337 | B2 * | 4/2012 | Manalang | B25H 3/06 211/70.6 |
| 8,210,548 | B1 | 7/2012 | Agyemang | |
| 8,215,650 | B2 | 7/2012 | Arceta et al. | |
| 8,258,973 | B2 | 9/2012 | Newkirk | |
| 8,286,977 | B2 | 10/2012 | Butler et al. | |
| 8,287,816 | B2 | 10/2012 | Kral | |
| 8,295,940 | B2 | 10/2012 | Sherman | |
| 8,482,252 | B2 * | 7/2013 | Byrne | G11B 33/122 320/113 |
| 8,696,075 | B1 * | 4/2014 | Rios | A47F 10/06 126/25 R |
| 2002/0013640 | A1 | 1/2002 | Phoon et al. | |
| 2003/0201697 | A1 | 10/2003 | Richardson | |
| 2005/0178298 | A1 | 8/2005 | Rossini | |
| 2005/0236940 | A1 | 10/2005 | Rockoff | |
| 2006/0219718 | A1 * | 10/2006 | Finnestad | A61B 50/362 220/254.3 |
| 2007/0018433 | A1 * | 1/2007 | Sinnamon | A61G 12/001 280/651 |
| 2007/0055116 | A1 | 3/2007 | Clark et al. | |
| 2007/0295627 | A1 * | 12/2007 | Hsieh | A47B 88/944 206/372 |
| 2008/0164792 | A1 * | 7/2008 | Goldberg | A47B 21/00 312/249.8 |
| 2008/0203861 | A1 * | 8/2008 | Wingate | A61G 12/001 312/209 |
| 2008/0265728 | A1 * | 10/2008 | Collins | A47B 47/0075 312/326 |
| 2008/0303389 | A1 | 12/2008 | Petrovich | |
| 2008/0316045 | A1 | 12/2008 | Sriharto et al. | |
| 2009/0261992 | A1 | 10/2009 | Song | |
| 2009/0267772 | A1 | 10/2009 | Dehnadi | |
| 2010/0213679 | A1 | 8/2010 | Smith et al. | |
| 2010/0228392 | A1 * | 9/2010 | Braun | A61G 12/001 700/242 |
| 2010/0264738 | A1 | 10/2010 | Murtha et al. | |
| 2010/0295430 | A1 * | 11/2010 | Cheng | B25H 3/028 312/249.11 |
| 2010/0312039 | A1 * | 12/2010 | Quirico | A61M 5/14 600/4 |
| 2011/0134601 | A1 * | 6/2011 | Sa | G06F 1/1632 361/679.43 |
| 2011/0172815 | A1 | 7/2011 | Kim | |
| 2012/0180789 | A1 | 7/2012 | Tobia et al. | |

FOREIGN PATENT DOCUMENTS

| | | |
|---|---|---|
| CN | 102481050 A | 5/2012 |
| JP | 63-102181 | 7/1988 |
| JP | 05-146474 | 6/1993 |
| JP | 2008-048786 A | 3/2008 |
| JP | 2011-218154 A | 11/2011 |
| WO | 2006074473 A2 | 7/2006 |
| WO | 2007/077609 A1 | 7/2007 |

OTHER PUBLICATIONS

Chinese Office Action dated Nov. 18, 2016 in corresponding Chinese Patent Appln. No. 2013106421052.
European Search Report EP13195238.4 dated Feb. 24, 2017.
Japanese Office Action dated Jul. 26, 2017 issued in corresponding JP Application No. 2013-248841.
Chinese Office Action dated Sep. 21, 2017 issued in corresponding Chinese Application No. 2013106421052.
Australian Examination Report dated Oct. 12, 2017 issued in corresponding Australian Application No. 2013257438.

* cited by examiner

SMART CART

CROSS-REFERENCE TO RELATED APPLICATIONS

This application claims the benefit of and priority to U.S. Provisional Patent Application No. 61/732,640, filed Dec. 3, 2012, the entire disclosure of which is incorporated by reference herein.

BACKGROUND

1. Technical Field

The present disclosure relates to a storage cart for surgical stapling products. More particularly, the present disclosure relates to an interactive storage and supply cart having electrical power and mounting capabilities for supporting communications devices, tablet type computers, recharging units and/or power sources for other electrically operated devices.

2. Background of Related Art

During many surgical procedures it is often necessary to employ multiple surgical instruments to properly perform the procedure. Many of these surgical instruments are modular and may include reloadable or disposable components specific to each instrument. This requires a management strategy to keep the surgical instruments and their related components separate to avoid confusion during surgery and avoid wasting time searching for correct instruments and associated components. Maintaining an accurate inventory of what is currently on hand may also become a problem.

Many modern surgical instruments now incorporate powered features that require rechargeable battery packs. Multiple battery packs and associated charges are required to be maintained in the operating room to avoid being faced with a depleted or faulty battery pack during an operation. Multiple chargers placed around the operating room may cause confusion leading to extended operation time and cause danger of tripping over multiple power cords.

More complex surgical procedures often require consultation with outside sources to obtain real time information about dealing with complications that may occur during the surgical procedure.

Therefore, it is desirable to provide a surgical device storage and supply cart capable of maintaining and organizing multiple surgical instruments and associated components. It is further desirable to provide a surgical device storage and supply cart having battery charging capabilities to ensure that fully operational battery packs are readily and safely available to the operating staff. It is still further desirable to provide a surgical device storage and supply cart having a docking station for receipt of computers for inventory management and instructional material or communication devices such as iPod™'s or iPad™'s to provide real time consultation with outside sources such as other surgeons or similar experts.

SUMMARY

There is disclosed a storage cart for storing, displaying and supplying surgical instruments and associated attachments. The storage cart generally includes a top storage assembly having at least two storage containers and a bottom storage assembly having at least one storage drawer. A shelf is positioned intermediate the top storage assembly and the bottom storage assembly and is affixed to the bottom storage assembly. A battery charging station is positioned on the shelf and may include a battery charger for receiving and charging a rechargeable battery and a battery charger holder to support the battery charger on the shelf. An electronic device docking station is positioned on the top storage assembly and is provided to receive electronic devices for tracking the contents of the cart as well as displaying product or surgical procedure information and providing real time communication with outside sources.

The top storage assembly includes a power strip for supplying power to the battery charging station and the electronic device docking station. In one embodiment, the at least two storage containers are of differing sizes. Multiple rows of differing size storage containers are provided to accommodate differing product package sizes. In a specific embodiment, the top storage assembly has a domed cover to prevent its use as a placement surface. This is to discourage placement of items on the top storage assembly and prevent those items from falling off the cart. The top storage assembly also has one or more document holders to support product and patient information and charts. In one embodiment, the top storage assembly has at least one cable lock strap to secure the docking station contents.

The shelf, positioned intermediate the top storage assembly and the bottom storage assembly, includes at least one storage tray for frequently used item and to collect personal items not previously removed prior to surgery.

The lower storage assembly includes a rear access panel to facilitate access to the at least one drawer for restocking. The lower storage assembly also includes at least one window to view the contents of the at least one storage drawer. The lower storage assembly further includes a wheel assembly to facilitate moving the storage cart. The wheel assembly may include one or more locking wheels or castors to secure the storage cart in place.

There is also disclosed a surgical device storage cart including a top storage assembly having a storage container and a bottom storage assembly having a storage drawer. A shelf is positioned intermediate the top storage assembly and the bottom storage assembly and includes at least one battery charger being positioned on the shelf. In one embodiment, at least one battery charger is positioned on a side of the shelf.

In an alternate embodiment, the at least one battery charger includes a first and a second battery charger, the first and second battery chargers positioned on opposite corners of the front of the shelf.

The storage cart further includes an electronic device docking station positioned on the shelf. The storage cart still further includes a power strip in electrical communication with the at least one battery charger and the electronic device docking station to provide power to the battery charger and docking station as well as other powered surgical devices.

There is still further disclosed a surgical device storage cart including a top storage assembly having a storage container, a bottom storage assembly having a storage drawer and a power strip positioned within the top storage assembly. In one embodiment, a battery charger is positioned on the top storage assembly. An electronic device docking station is also positioned on the top storage assembly. In a specific embodiment, the top storage assembly has a domed cover and the battery charger is mounted on the domed cover. The storage cart includes at least one document holder positioned on the top storage assembly.

DESCRIPTION OF THE DRAWINGS

Various embodiments of the presently disclosed interactive surgical product storage, supply and display carts or "smart carts" are disclosed herein with reference to the drawings, wherein.

DETAILED DESCRIPTION OF EMBODIMENTS

Embodiments of the presently disclosed product storage, supply and display carts or "smart carts" will now be described in detail with reference to the drawings wherein like numerals designate identical or corresponding elements in each of the several views. As is common in the art, the term 'proximal" refers to that part or component closer to the user or operator, i.e. nurse, surgeon or physician, while the term "distal" refers to that part or component further away from the user.

Referring to FIGS. 1-13, and initially to FIGS. 1-8, there is illustrated one embodiment of an interactive surgical instrument storage, display and supply cart or smart cart 10 for use in a surgical operating room. While not specifically shown, smart cart 10 is provided to store, display and supply ENDO GIA™, TRI-STAPLE™ and iDRIVE™ Surgical stapling products, including instruments and reloading components to surgeons and their assistants in the operating room. Additionally, smart cart 10 provides capabilities for supporting and powering computer and display devices such as, for example, iPad™'s, iPod™'s, etc. as well as charging and supplying fully charged iDrive™ Ultra batteries for use with iDrive™ surgical instruments. The smart cart 10 typically does not have to be sterile and may be kept in the central core. In the event the smart cart 10 is moved outside the central core a drape (not shown) is provided to cover the cart.

Figure 1:
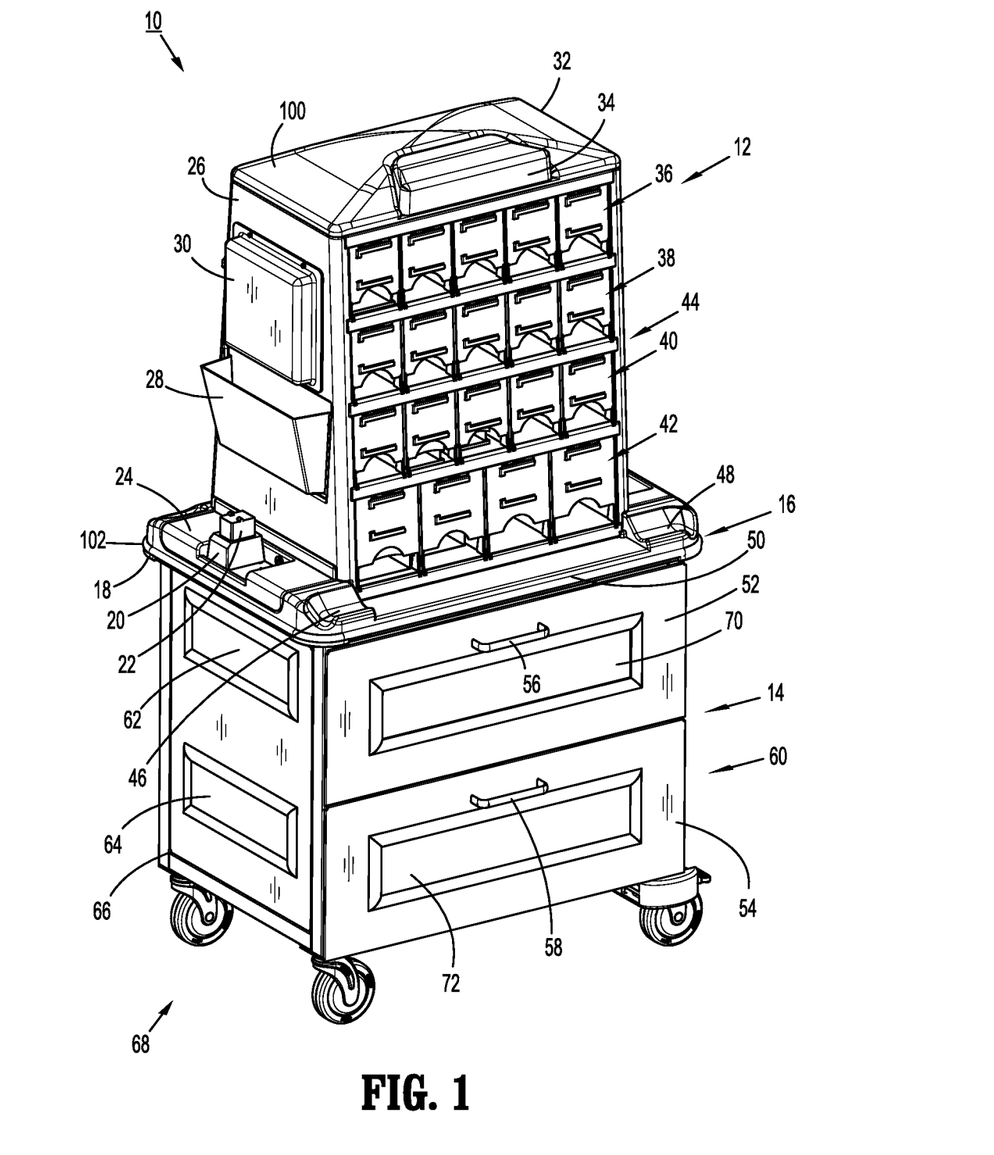
FIG. 1 is a perspective view of one embodiment of a smart cart for use in a surgical operating room.

Referring to FIG. 1, smart cart 10 generally includes a top storage assembly 12, a bottom storage assembly 14 and an intermediate shelf or shelf portion 16 positioned between top storage assembly 12 and bottom storage assembly 14. A first side edge 18 of shelf portion 16 contains a removable battery charger 20 for recharging and supplying fully charged battery packs 22. Battery charger 20 may be mounted directly to first side edge 18 of shelf portion 16 or may be positioned in a removable charger holder 24 positioned on first side edge 18. Use of a removable charger holder 24 allows the users to pre-configure smart cart 10 based on the specific powered surgical devices to be used.

Figure 3:
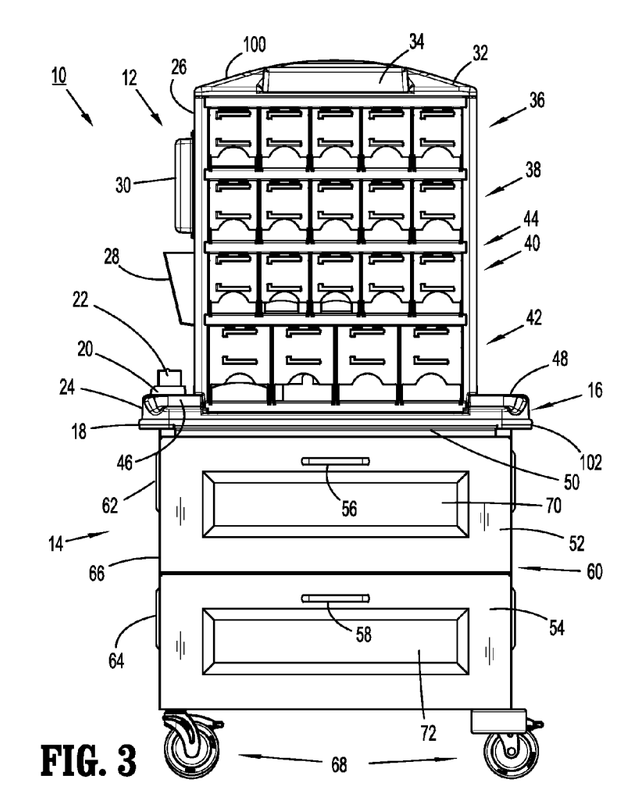
FIG. 3 is a front plan view of the smart cart.
Figure 6:
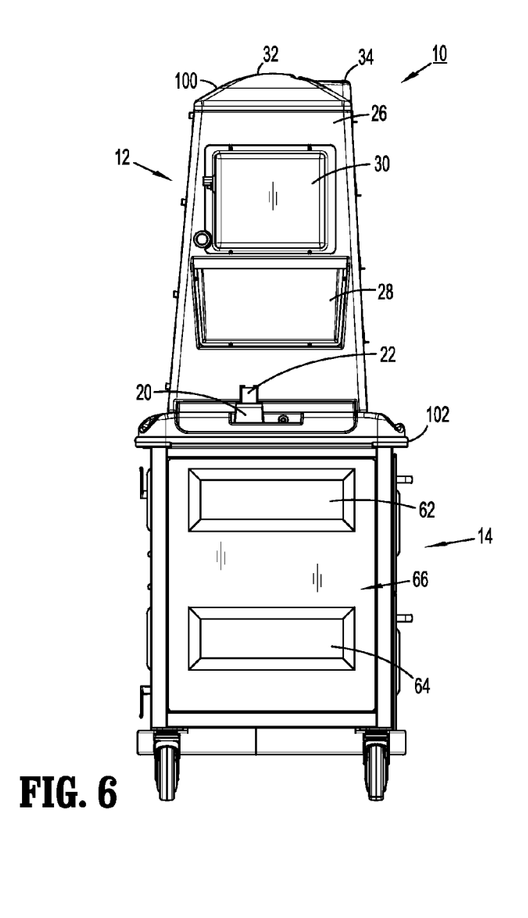
FIG. 6 is an opposite side plan view of the smart cart.

With reference to FIGS. 1, 3 and 6, a first side panel 26 of top storage assembly 12 is provided with a document holder 28 which can be used for various purposes, such as, for example, instrument inventory and instructions, patient records, etc. Document holder 28 may also be used to retain electronic device and communication instructions and relevant contact phone/email/texting numbers and addresses. First side panel 26 of top storage assembly 12 is also provided with an electronic device mount or docking station 30 which allows the users to connect and view various tablet type computers, access electronic communication via cellular, Wi Fi and/or Bluetooth devices and view display devices. This allows the surgeon to view surgical product and procedure information and/or consult with external sources in real time. Top storage assembly additionally includes a top cover 32 which is provided with an information retaining cap 34. Cap 34 is provided to display specific patient charts or other documents for immediate viewing.

Figure 12:
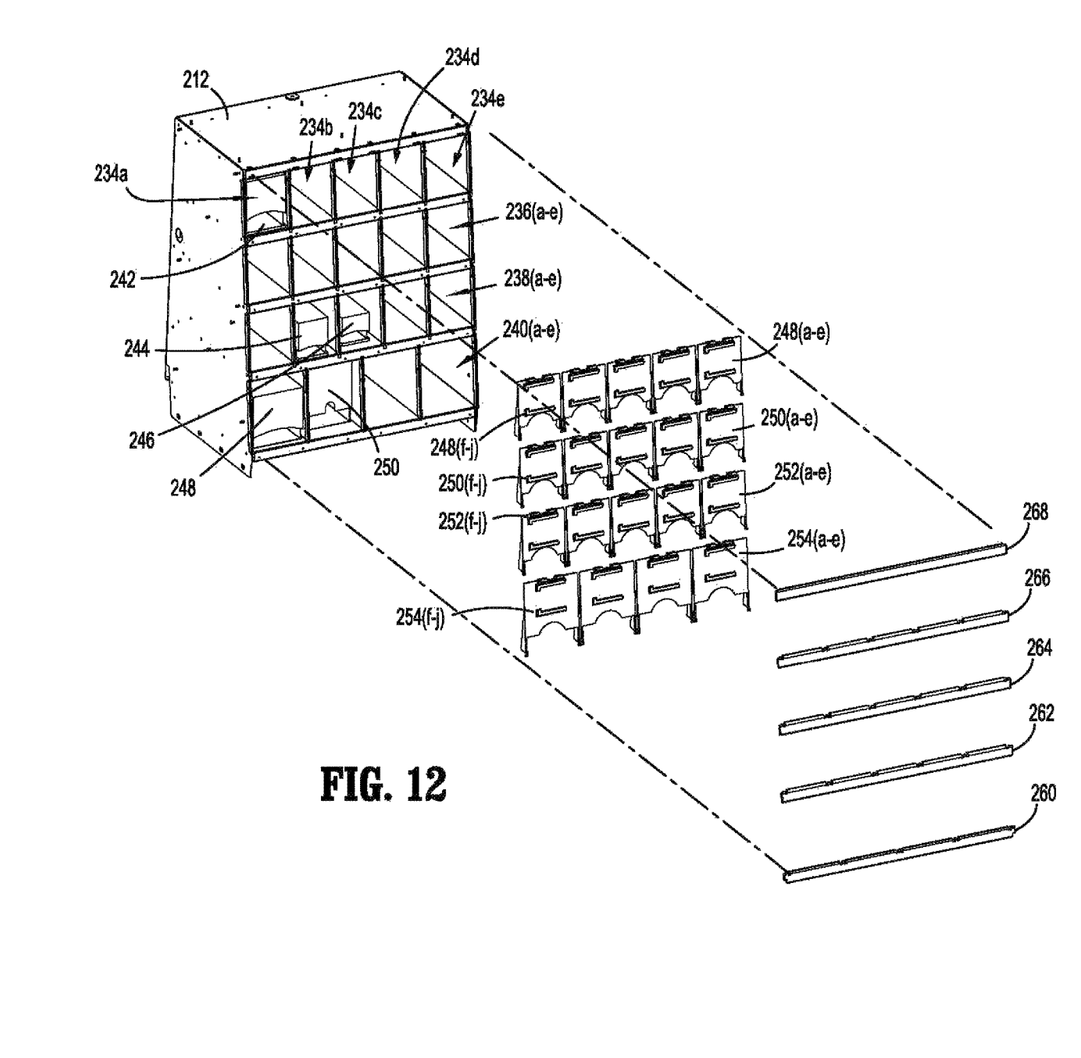
FIG. 12 is a further perspective view, with parts separated, of the top storage assembly.

Referring to FIGS. 1 and 3, top storage assembly 12 is more specifically provided to store and display various surgical stapling reloading components (see FIG. 12). Multiple rows of various size storage containers 38, 40, 42 and 44 are provided in a front side 44 of top storage assembly 12 to retain, identify and/or display the components as described in more detail hereinbelow.

A pair of personal effects storage trays 46 and 48 are provided on a front side 50 of shelf portion 16 to retain patient and provider items not previously removed prior to surgery.

With continued reference to FIGS. 1 and 3, bottom storage assembly 14 includes upper and lower drawers 52 and 54, having respective handles 56 and 58, in a front side 60 of bottom storage assembly 14. Upper and lower drawers 52 and 54 are provided to retain various surgical instruments. Upper and lower viewing windows 62 and 64 are provided in a first side 66 of bottom storage assembly 14 to facilitate viewing the contents of upper and lower drawers 52 and 54. In order to manipulate storage cart 10 within the operating room, bottom storage assembly 14 is provided with a wheel assembly 68, described in more detail hereinbelow. Upper and lower drawers 52 and 54 are provided with front plates 70 and 72 which may be transparent to view the contents or may be used to support labels or other indicia describing the contents of upper and lower drawers 52 and 54.

Figure 2:
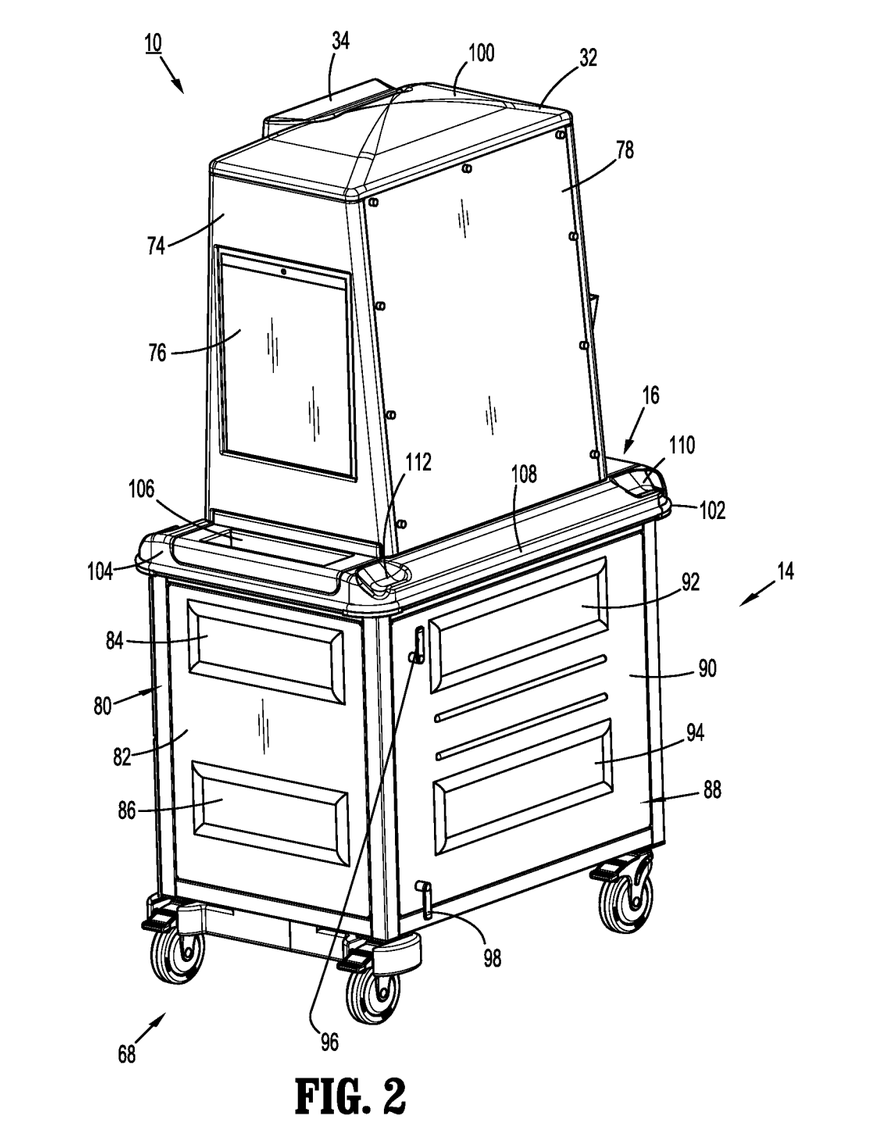
FIG. 2 is another perspective view of the smart cart.
Figure 4:
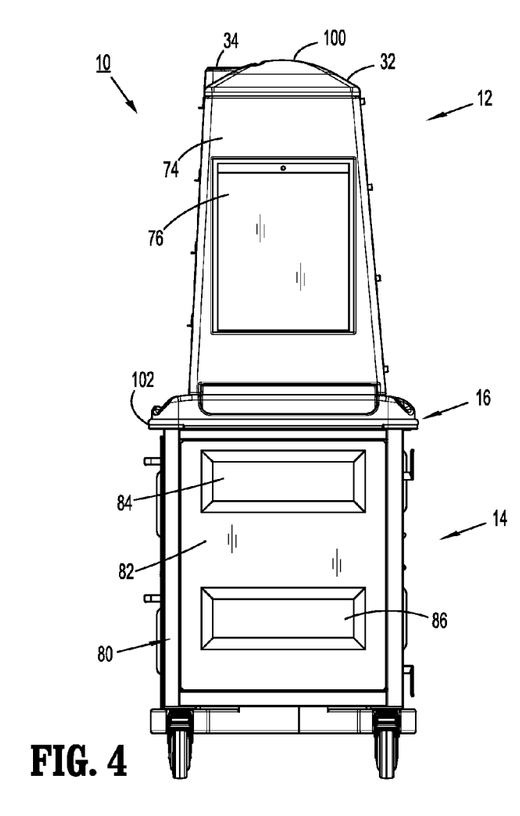
FIG. 4 is a side plan view of the smart cart.

Referring now to FIGS. 2 and 4, a second side panel 74 of top storage assembly 12 is also provided with a document holder or sleeve 76 for retention of patient records, etc. Top storage assembly 12 additionally includes a removable back panel 78.

Bottom storage assembly 14 includes a frame 80. A second side 82 of bottom storage assembly 14 also includes viewing windows 84 and 86 to view the contents of bottom storage assembly 14.

Figure 5:
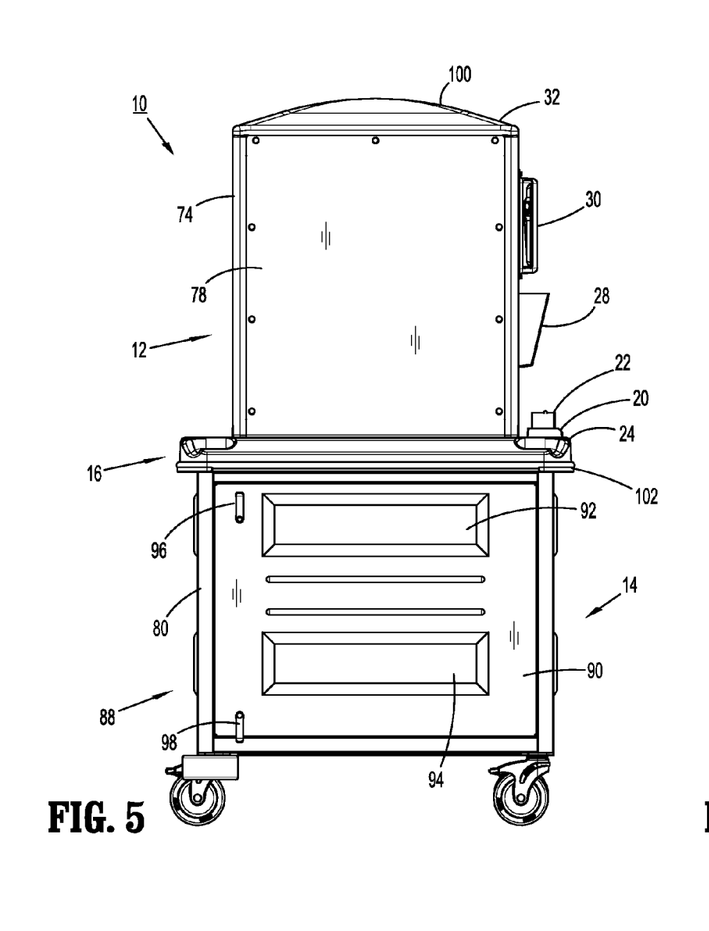
FIG. 5 is a rear plan view of the smart cart.

Referring to FIGS. 2 and 5, a back side 88 of bottom storage assembly 14 is provided with a removable door panel 90 to facilitate restocking upper and lower drawers 52 and 54 (FIG. 1). Removable door panel 90 includes viewing windows 92 and 94 for viewing the contents of upper and lower drawers 52 and 54, respectively. Lock handles 96 and 98 are provided on door panel 90 and engage frame 80 to secure door panel 90 to frame 80.

With reference to FIGS. 1-6, top cap 32 has a domed outer surface 100 to prevent its use as a tray or surface upon which items may be inadvertently placed and knocked or fall off. In order to prevent damage to smart cart 10, shelf portion 16 includes a flexible, polymeric or rubber peripheral edge or bumper 102.

Figure 7:
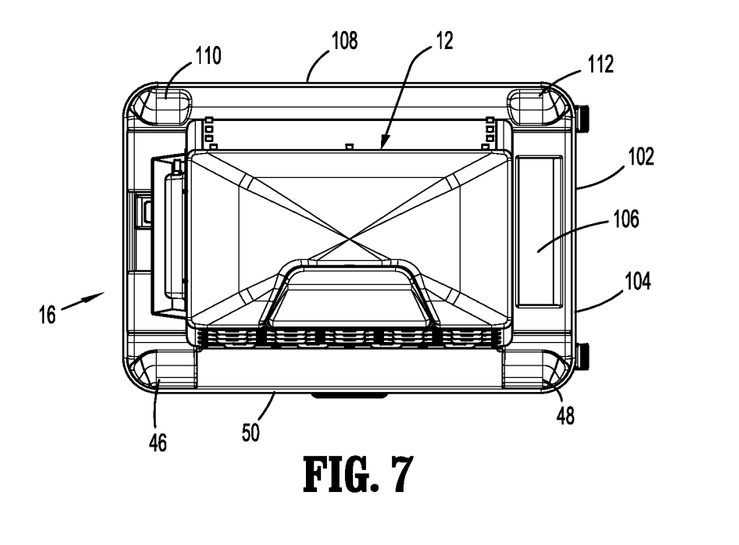
FIG. 7 is a top plan view of the smart cart.

Referring now to FIGS. 2 and 7, shelf portion 16 includes a second side edge 104 having an items tray 106 for receipt of various items frequently used during the surgical procedure. A back side 108 of shelf portion 16 is also provided with a pair of personal effects pockets or trays 110 and 112 similar to trays 46 and 48 in front side 50 of shelf portion 16.

Figure 8:
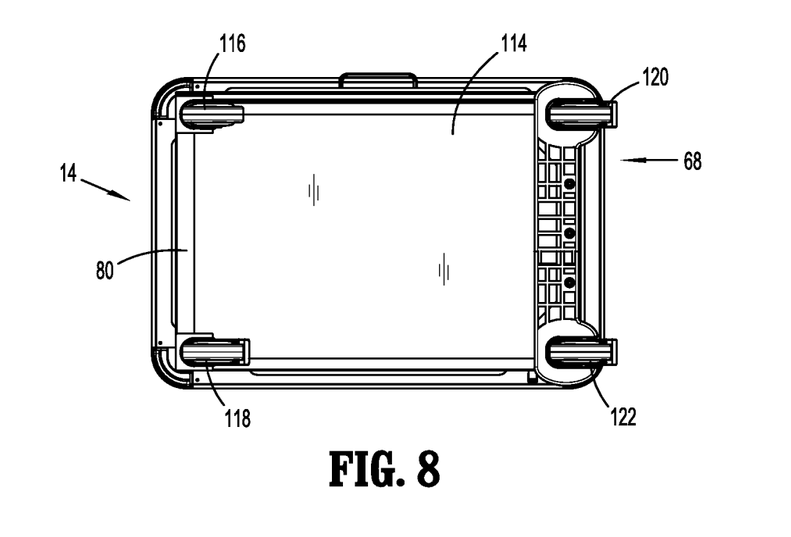
FIG. 8 is a bottom plan view of the smart cart.

Referring for the moment to FIG. 8, it can be seen that bottom storage assembly 14 includes a floor panel 114 on frame 80. Additionally, wheel assembly 68 includes a pair of front swiveling wheels 116 and 118 and a pair of rear locking wheels 120 and 122.

Figure 9:
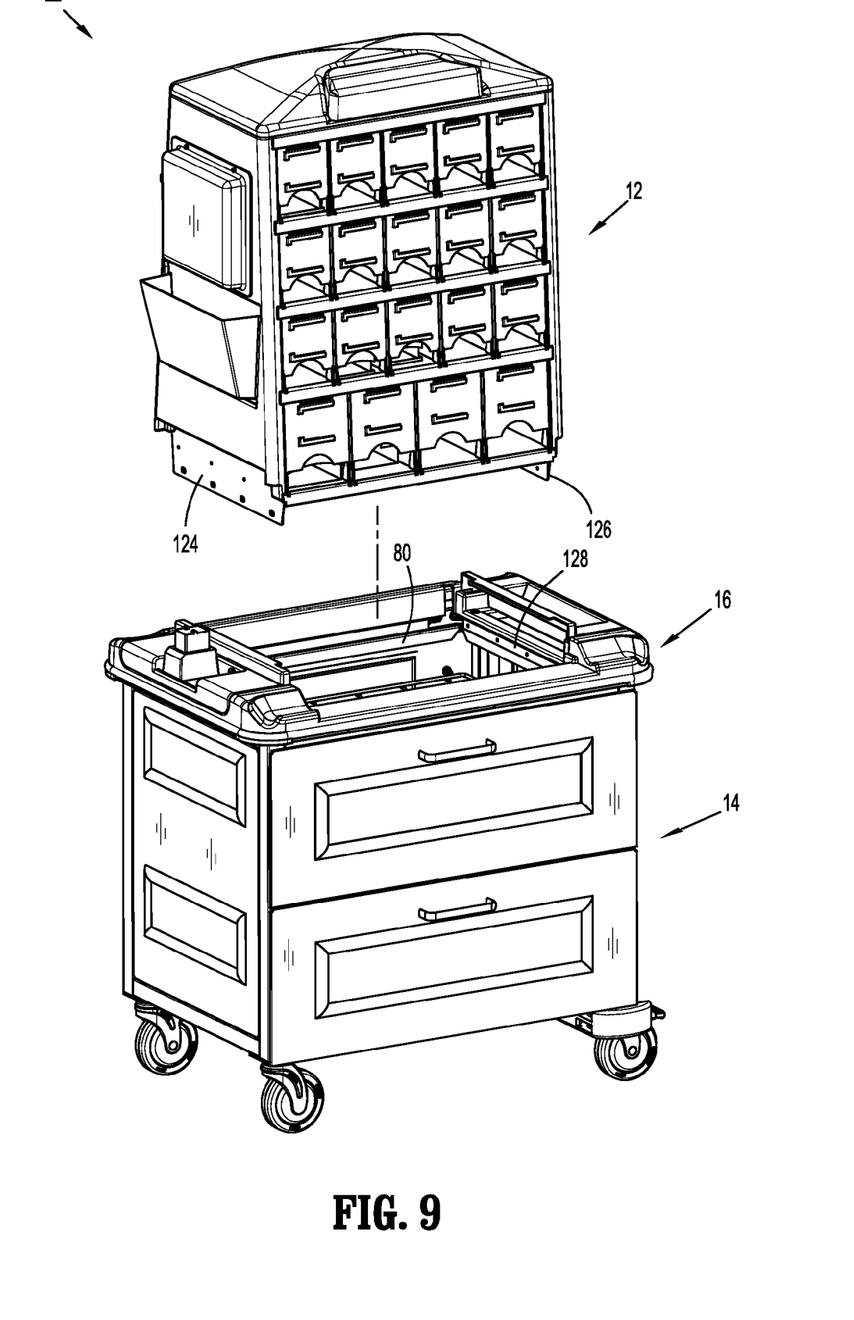
FIG. 9 is a perspective view of the smart cart with top and bottom storage assemblies separated.

Referring now to FIGS. 9-13, the construction features of smart cart 10 will now be described. Referring initially to FIG. 9, a fully assembled top storage assembly 12 and fully assembled bottom storage assembly 14 may be provided separately so that the components can be interchanged depending on use. Shelf portion 16 is provided with bottom storage assembly 14 to supply the correct batteries 22 for the surgical instruments contained in bottom storage assembly 14. Top storage assembly 12 includes a pair of mounting plates 124 and 126 which are configured to engage and be secured to an inside edge 128 of frame 80 of bottom storage assembly 14.

Figure 10:
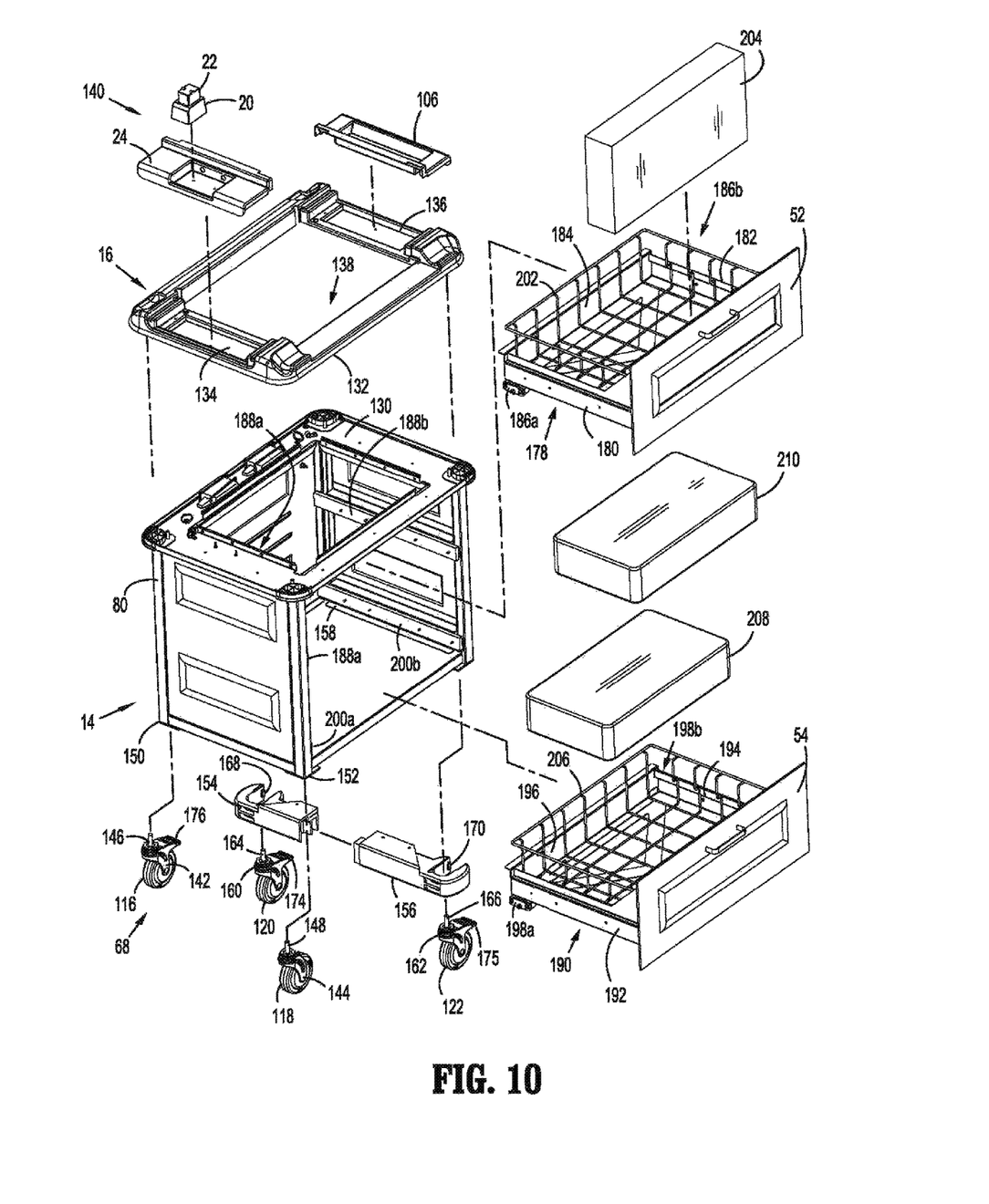
FIG. 10 is a perspective view, with parts separated, of the bottom storage assembly.

Referring to FIG. 10, shelf portion 16 is mounted to a rectangular upper plate 130 provided on frame 80 of bottom storage assembly 14. Specifically, an outer frame 132 of shelf portion, which includes an opening 138 defined therethrough, engages upper plate 130 of bottom storage assembly 14 and is secured thereto. As shown, charger holder 24 is mounted in a recess 134 of outer frame 132 and item tray 106 is mounted in a recess 136 of outer frame 132. Battery charger 20 and charger holder 24 form a charging assembly 140 mounted on shelf portion 16.

As noted hereinabove, wheel assembly 68 includes swiveling front wheels 116 and 118 and locking rear wheels 120 and 122. Front wheels 116 and 118 are mounted on wheel frames 142 and 144 and include respective mounting pins 146 and 148. Pins 146 and 148 are rotatably mounted in first and second lower front corners 150 and 152, respectively, of frame 80 of bottom storage assembly 14. In order to secure rear locking wheels 120 and 122 from swiveling, bottom storage assembly 14 includes a pair of mounting brackets 154 and 156 which are affixed to a lower rear edge 158 of frame 80.

Locking wheels 120 and 122 also include frames 160 and 162 and respective mounting pins 164 and 166. Pins 164 and 166 extend through cutouts in brackets 154 and 156 and engage lower rear edge 158 of frame 80. Wheels 120 and 122 are positioned within cutouts 168 and 170 formed in brackets 154 and 156 to thereby prevent wheels 120 and 122 from swiveling. In order to secure smart cart 10 and keep locking wheels 120 and 122 from rotating, lock levers 174 and 175 are provided on frames 160 and 162 and function in known manner to lock and unlock wheels 120 and 122 from rotation. Additionally, a third lock lever 176 may be provided on one of the front wheels, such as frame 142 of front wheel 116, to further secure smart cart 10 against movement.

As noted above, upper and lower drawers 52 and 54 are provided to store surgical instruments. Upper drawer 52 is slidably mounted to frame 80 of bottom storage assembly 14 and includes a drawer frame 178 having a first side 180, a second side 182 and a back 184. Rollers 186*a,b* are mounted on first and second sides 180,182 of drawer frame 178 and ride on tracks 188*a,b*, respectively, mounted on frame 80. Likewise, lower drawer 54 is slidably mounted to frame 80 and includes a drawer frame 190 having a first side 192, a second side 194 and a back 196. Rollers 198*a,b* are mounted on first and second sides 192, 194, respectively, and ride on tracks 200*a,b* mounted on frame 80.

An upper wire basket 202 is provided in upper drawer 52 to retain a sterilized product package 204. Sterilized product package 204 is configured and dimensioned to contain a sterilized surgical instrument (not shown). Similarly, a lower wire basket 206 is provided in lower drawer 54 and is configured and dimensioned to contain one or more sterilized product packages 208 and 210. Upper and lower wire baskets 202 and 206 are easily removed for refilling by opening door panel 90 (FIG. 2) to access upper and lower drawers 52 and 54 from the rear of smart cart 10.

Figure 11:
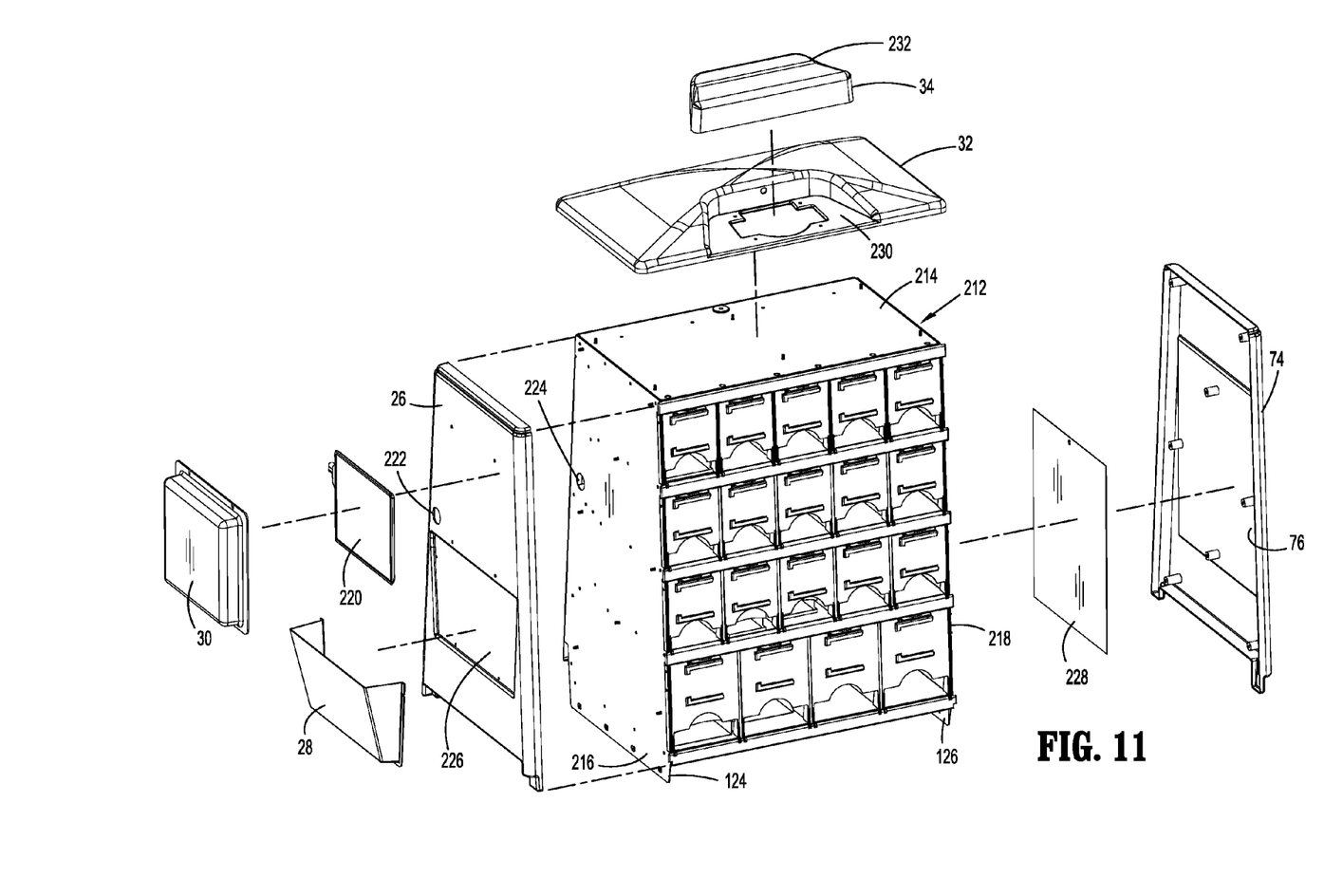
FIG. 11 is a perspective view, with parts separated, of the top storage assembly.
Figure 13:
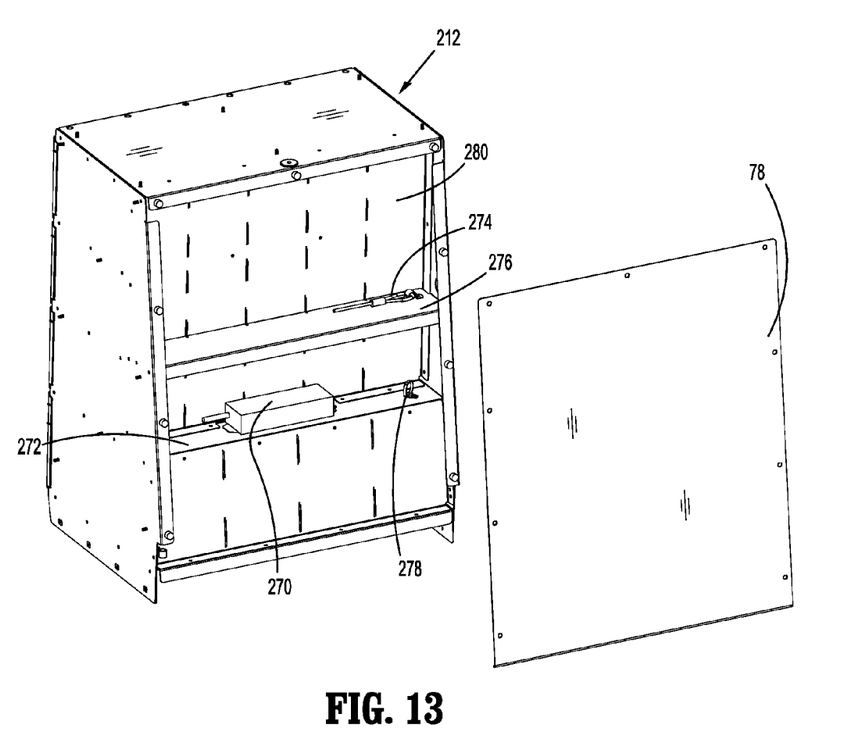
FIG. 13 is a perspective view, with back panel removed, of the top storage assembly revealing a power strip.

Referring to FIGS. 11-13, and initially to FIG. 11, top storage assembly 12 includes an internal box 212 having a top 214 and first and second sides 216 and 218. Mounting plates 124 and 126 extend from first and second sides 216 and 218. First side panel 26 overlies and is affixed to first side 216 of internal box 212. A secure back case 220 is affixed to first side panel 26 and is provided to mount docking station 30. An opening 226 is defined in the first side panel 26 and is provided to mount document holder 28. Holes 222 and 224 formed through first side panel 26 and first side 216 allow for communication and/or power cables (not shown) to extend from docking station 30 to the interior of internal box 212.

Second side panel 74 overlies and is affixed to second side 218 of internal box 212. A document protector 228 is provided adjacent document holder 76. Top cover 32 overlies and is affixed to top 214 of internal box 212 and includes a recess 230 for mounting cap 34. Cap 34 is provided with a clip or slot 232 to hold patient related data charts. Alternatively, cap 34 can be configured to retain communications or display devices.

Turning now to FIG. 12, internal box 212 defines storage containers of varying sizes 234 (*a-e*), 236 (*a-e*), 238 (*a-e*) and 240 (*a-e*) corresponding to storage containers 36, 38, 40 and 42 disclosed hereinabove. Storage containers, 234-240 are provided to retain various surgical instrument refills such as, for example, product boxes 242, 244, 246, 248 and 250. The product boxes may contain sterilized small, medium or large components as well as dual and radial components in the form of disposable loading units or "DLU's", etc.

Pivotal face plates 248 (*a-e*), 250 (*a-e*), 252 (*a-e*) and 254 (*a-e*) are provided to cover storage containers 234-240, respectively. The disclosed pivotal face plates within a row may pivot independently or be linked together. For example, pivotal face plates 248*a*, 248*b*, 248*c*, 248*d* and 248*e* may pivot independently to reveal storage containers 234 (*a-e*) individually or pivot simultaneously to present the contents of storage containers 234 (*a-e*) all at the same time.

Pivotal face plates 248-254 additionally include respective card holders 248 (*f-j*), 250 (*f-j*), 252 (*f-j*) and 254 (*f-j*) for retaining informational product cards (not shown) specific to the contents of the respective storage containers 234-240.

The product cards may be color coded or otherwise marked to quickly and easily coordinate the contents with specific surgical instruments.

In order to pivot pivotal face plates 248, 250, 252 and 254, internal box 212 is provided with strips of hinges 260, 262, 264 and 266 which mount pivotal face plates 254, 252, 250 and 248, respectively. In addition, strip of hinges 262-266 form a surface against which pivotal face plates 254, 252 and 250 secure in snap fit fashion. A top bar 268 is provided on internal box 212 above storage containers 234 to allow pivotal face plates 248 to close and secure in snap fit fashion.

Referring to FIG. 13, internal box 212 mounts removable back panel 78. A power strip 270 is provided within internal box 212 to power battery charger 20 and electrical components mounted to docking station 30 (FIG. 1). While not specifically shown, power strip 270 has a power cable extending through holes 222 and 224 in first side panel 26 and first side 216 and a second power cable having a male plug for attachment to an external power source. Power strip 270 is mounted on a first shelf 272 within internal box 212. Internal box 212 includes a lock cable 274 secured to a second shelf 276. A second lock cable 278 is secured to first shelf 272. First and second lock cables 274 and 278 are provided to secure electrical components mounted in docking station 30. In order to prevent contamination of items retained within storage containers 234-240, an internal divider 280 is provided between storage containers 234-240 and removable back panel 78. Power strip 270 may additionally include plug outlets for powering other surgical devices. This can reduce power cord clutter in the operating room. In this manner, smart cart 10 provides a complete system for storage of various surgical instruments and disposable components.

Figure 14:
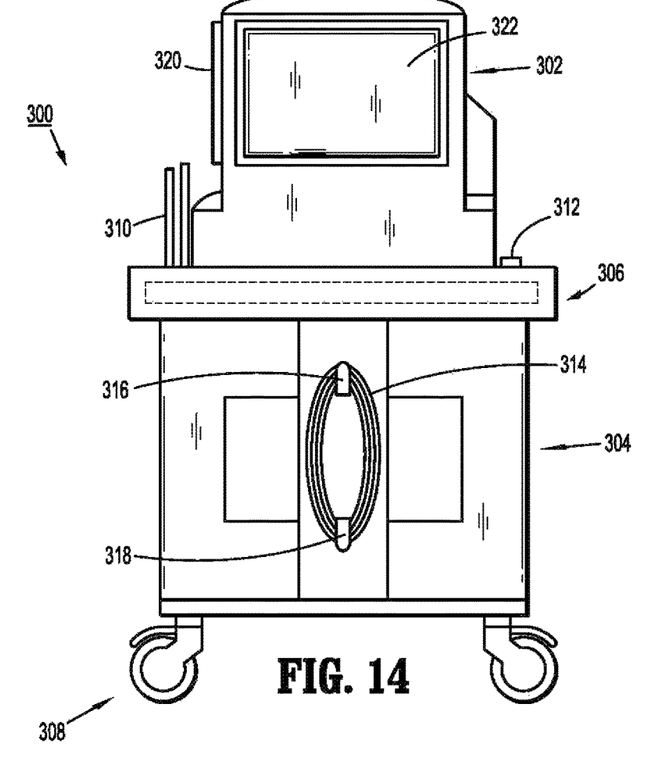
FIG. 14 is rear plan view of an alternate embodiment of a smart cart.
Figure 15:
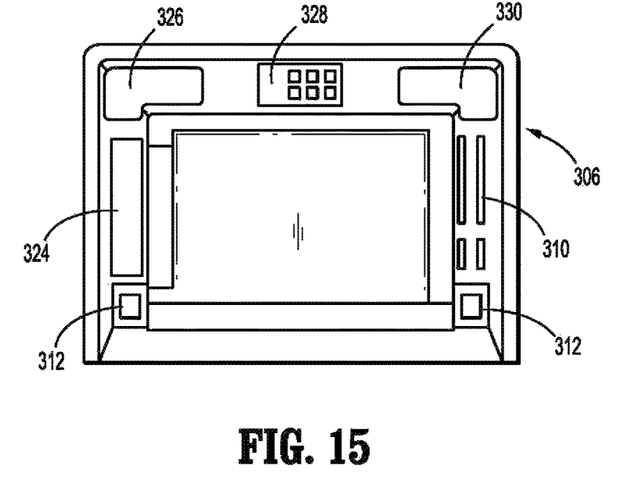
FIG. 15 is a top plan view of the smart cart of FIG. 14.

Referring now to FIGS. 14 and 15, there is disclosed an alternate embodiment of a smart cart 300. Smart cart 300 is similar to smart cart 10 described hereinabove and includes a top storage assembly 302, a bottom storage assembly 304 and an intermediate shelf portion 306 affixed to and forming a part of bottom storage assembly 304. A wheel assembly 308 similar to wheel assembly 68 described above is provided on bottom storage assembly 304. In this embodiment, an electronics docking station 310 is provided on intermediate shelf portion 306. Battery charger(s) 312 are also provided on shelf portion 306.

With specific reference to FIG. 14, document holders 320 and 322 are provided on top storage assembly 302 and a power cable 314 is provided and is mounted on brackets 316 and 318 on bottom storage assembly 304. As shown in FIG. 15, docking station 310 and power chargers 312 are mounted on shelf portion 306. Shelf portion 306 additionally includes a storage tray 324 and personal effects trays 326, 328 and 330.

Figure 16:
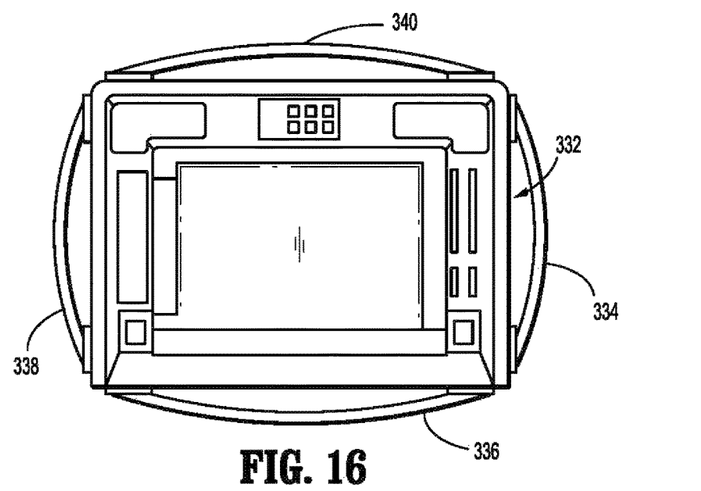
FIG. 16 is a top plan view of an alternate embodiment of an intermediate shelf portion for use with the disclosed smart carts.

Turning for the moment to FIG. 16, there is disclosed an alternate intermediate shelf portion 332 for use with smart cart 300. Shelf portion 332 is provided with sculpted handles 334, 336, 338 and 340 to facilitate manipulating smart cart 300 in the operating room and throughout the hospital for storage and restocking.

Figure 17:
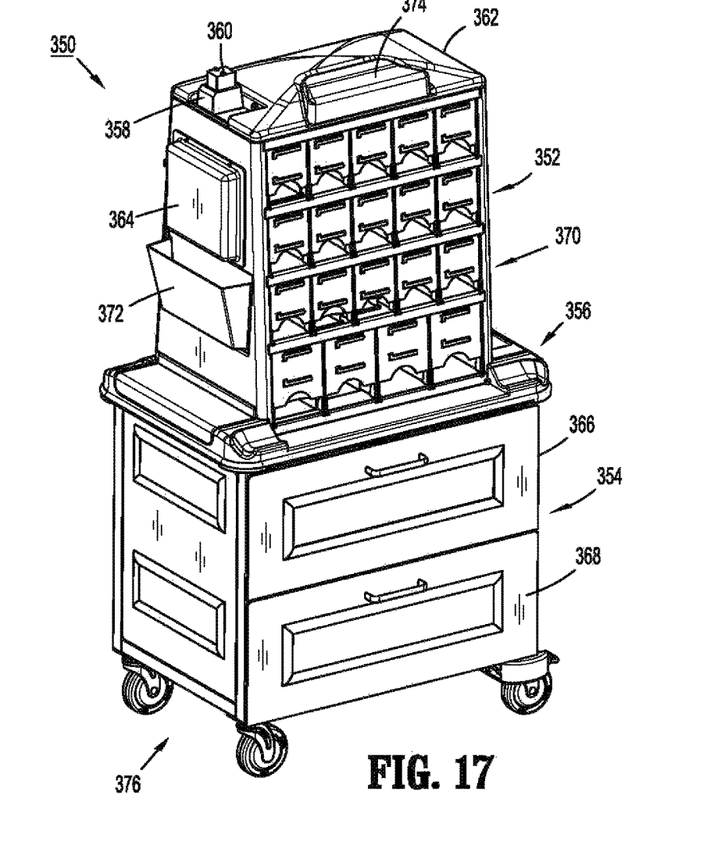
FIG. 17 is a perspective view of a further alternate embodiment of a smart cart.

Referring now to FIG. 17, there is disclosed a further embodiment of a smart cart 350 having a top storage assembly 352, a bottom storage assembly 354 and an intermediate shelf portion 356. Unlike prior embodiments, in this embodiment, a battery charger 358 for receiving battery 360 is mounted on top storage assembly 352 as opposed to shelf portion 356. Specifically, battery charger 358 is mounted on a top cover 362 of top storage assembly 352. A docking station 364 is also mounted on top storage assembly 352. Top storage assembly 352 and bottom storage assembly 354 are otherwise similar to top and bottom storage assemblies 12 and 14 of smart cart 10 described hereinabove. For example, bottom storage assembly 354 includes upper and lower drawers 366 and 368 for storage of surgical instruments and top storage assembly 352 includes multiple storage containers 370 for storage of reusable or disposable components. Document holder 372 and 374 are provided to retain informative materials and patient information while a wheel assembly 376 facilitates moving smart cart 350.

It will be understood that various modifications may be made to the embodiments disclosed herein. For example, multiple docking stations may be provided to accommodate devices individually dedicated to product management, communications and display of materials. Further, the disclosed storage containers and/or drawers may be sealed to receive hazardous waste material. Additionally, display screens may be provided to communicate with devices inserted into the docking station and provide a larger viewing screen. Therefore, the above description should not be construed as limiting, but merely as exemplifications of particular embodiments. Those skilled in the art will envision other modifications within the scope and spirit of the claims appended hereto.

The invention claimed is:

1. A surgical device storage cart comprising:
a top storage assembly having an internal box defining at least two storage containers, and including a first side panel, a second side panel, and a domed cover affixed to the internal box;
a bottom storage assembly having at least one storage drawer;
a shelf intermediate the top storage assembly and the bottom storage assembly and affixed to the bottom storage assembly, the shelf including an outer frame having a fixed outer perimeter and an inner perimeter defining a central opening therein, the outer frame including first and second sides extending laterally beyond the first and second side panels of the top storage assembly;
a battery charging station positioned on the shelf; and
an electronic device docking station positioned on an outer surface of the top storage assembly.

2. The storage cart as recited in claim 1, wherein the top storage assembly includes a power strip for supplying power to the battery charging station and the electronic device docking station.

3. The storage cart as recited in claim 2, wherein the at least two storage containers are of differing sizes.

4. The storage cart as recited in claim 2, wherein the top storage assembly has a document holder.

5. The storage cart as recited in claim 2, wherein the top storage assembly has at least one cable lock strap to secure docking station contents to the electronic device docking station.

6. The storage cart as recited in claim 2, wherein the shelf includes at least one storage tray.

7. The storage cart as recited in claim 2, wherein the bottom storage assembly includes a rear access panel.

8. The storage cart as recited in claim 2, wherein the bottom storage assembly includes at least one window to view the contents of the at least one storage drawer.

9. The storage cart as recited in claim 2, wherein the bottom storage assembly includes a wheel assembly to facilitate moving the storage cart.

10. The storage cart as recited in claim 1, wherein the bottom storage assembly includes a frame and the at least one storage drawer is slidably mounted to the frame, and the top storage assembly includes a pair of mounting plates extending through the central opening defined in the outer frame of the shelf and secured to an inside edge of the frame of the bottom storage assembly.

11. The storage cart as recited in claim 1, wherein one of the at least two storage containers defines an opening in a front side of the top storage assembly.

12. The storage cart as recited in claim 11, wherein the top storage assembly includes a pivotable face plate on the front side thereof to cover the opening.

13. The surgical device storage cart as recited in claim 1, wherein the electronic docking station is positioned on the first side panel of the top storage assembly.

14. The surgical device storage cart as recited in claim 1, wherein the top storage assembly is disposed over the central opening of the shelf such the outer frame of the shelf extends around the entire periphery of the top storage assembly.

15. The surgical device storage cart as recited in claim 1, wherein the outer frame of the shelf includes recesses defined therein, each of the recesses configured to removably receive the battery charging station or an item tray therein.

\* \* \* \* \*

UNITED STATES PATENT AND TRADEMARK OFFICE
CERTIFICATE OF CORRECTION

PATENT NO. : 9,887,562 B2  
APPLICATION NO. : 14/064388  
DATED : February 6, 2018  
INVENTOR(S) : Racenet et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 281 days.

Signed and Sealed this

Twenty-fifth Day of September, 2018

Andrei Iancu  
*Director of the United States Patent and Trademark Office*